United States Patent
Rogers et al.

(10) Patent No.: US 8,535,280 B2
(45) Date of Patent: Sep. 17, 2013

(54) PRESSURE BASED REFILL STATUS MONITOR FOR IMPLANTABLE PUMPS

(75) Inventors: Charles Randall Rogers, Maple Grove, MN (US); Scott L. Kalpin, Harris, MN (US); William J. Mitchell, Eden Prairie, MN (US)

(73) Assignee: Medtronic, In, Minneapolis, MO (US)

( * ) Notice: Subject to any disclaimer, the term of this patent is extended or adjusted under 35 U.S.C. 154(b) by 406 days.

(21) Appl. No.: 12/199,536

(22) Filed: Aug. 27, 2008

(65) Prior Publication Data

US 2009/0082757 A1 Mar. 26, 2009

Related U.S. Application Data

(60) Provisional application No. 60/975,286, filed on Sep. 26, 2007.

(51) Int. Cl.
*A61M 37/00* (2006.01)

(52) U.S. Cl.
USPC .................................. 604/288.01; 604/891.1

(58) Field of Classification Search
USPC ....................... 604/288.01, 65, 67, 131, 890.1
See application file for complete search history.

(56) References Cited

U.S. PATENT DOCUMENTS

| | | | |
|---|---|---|---|
| 4,561,298 A | 12/1985 | Pond | |
| 6,321,597 B1 | 11/2001 | Demers et al. | |
| 6,562,001 B2 | 5/2003 | Lebel et al. | |
| 2002/0087116 A1 | 7/2002 | Hartlaub | |
| 2002/0161328 A1 | 10/2002 | Rogers | |
| 2004/0249336 A1 | 12/2004 | Faries et al. | |
| 2005/0075624 A1* | 4/2005 | Miesel | 604/505 |
| 2005/0187515 A1* | 8/2005 | Varrichio et al. | 604/67 |
| 2006/0089619 A1 | 4/2006 | Ginggen | |
| 2006/0149220 A1 | 7/2006 | Ullestad et al. | |
| 2007/0239381 A1 | 10/2007 | Ginggen et al. | |
| 2008/0306466 A1* | 12/2008 | Shelton et al. | 604/502 |

FOREIGN PATENT DOCUMENTS

| | | | |
|---|---|---|---|
| EP | 0622615 A1 | * | 2/1994 |
| EP | 0622615 A1 | | 11/1994 |
| EP | 1649884 A1 | | 4/2006 |
| WO | 2007041471 A2 | | 4/2007 |
| WO | 2008121421 A1 | | 10/2008 |

OTHER PUBLICATIONS

International Search Report issued Jan. 22, 2009 in the co-pending PCT application No. PCT/US08/074548.

* cited by examiner

*Primary Examiner* — Kevin C Sirmons
*Assistant Examiner* — Brandy S Lee
(74) *Attorney, Agent, or Firm* — Mueting Raasch Gebhardt PA

(57) ABSTRACT

The present invention includes systems and methods for detecting fluid flow into or out of a port chamber or a reservoir of an implantable medical device utilizing a pressure sensor. The system detects characteristic pressure profiles associated with fluid flowing into the medical device, out of the medical device, and also whether one or both of the port chamber or reservoir are substantially empty or substantially full. In addition, the present invention may generate a sensory cue to a clinician to indicate the fluid status.

6 Claims, 12 Drawing Sheets

US 8,535,280 B2

PRESSURE BASED REFILL STATUS MONITOR FOR IMPLANTABLE PUMPS

RELATED APPLICATION

This application claims priority to provisional U.S. application Ser. No. 60/975,286, filed Sep. 26, 2007.

FIELD

The present invention relates to implantable medical devices for delivering fluid to a target site within a patient. More particularly, it relates to systems, devices and methods for sensing and monitoring the withdrawal and filling of fluid into the medical device.

BACKGROUND

A variety of implantable infusion devices are available for treating patients. For example, implantable infusion devices are used for delivering therapeutic substances to a target location of a patient. The implantable infusion devices are implanted subcutaneously in a convenient location in the patient. An infusion catheter is connected to an outlet of the device and positioned in the patient to allow delivery to the target location. A therapeutic substance may then be introduced percutaneously into a reservoir of the implanted device by inserting a needle into a port assembly of the device and delivering a fluid containing the therapeutic substance to the device via the needle.

Because the device is implanted within the patient and cannot be seen directly, care must be taken to monitor the withdrawal and filling of the therapeutic substance into the reservoir. For example, when removing a drug from the reservoir it is advantageous to know when the all or substantially all of the drug has been removed. Moreover, it is additionally advantageous to know when the reservoir has been filled with the new drug.

A need therefore exists for a system capable of detecting the flow of therapeutic substance out of and into the reservoir of an implantable delivery device. A need also exists for indicating where the reservoir is substantially or completely full or empty.

SUMMARY

The present disclosure describes, inter alia, systems, devices and methods that can be used to monitor the flow of a therapeutic substance, or other material such as a wash or rinse aid, into the reservoir of an implantable infusion device. The methods, systems and devices may be used to detect the flow into and out of the reservoir of the implantable infusion device. Moreover, the methods, systems and devices may be able to indicate a status such as "full" or "empty" when the material is reservoir is completely emptied or filled.

One embodiment may include a method for detecting fluid flow into and out of an implantable infusion device, the device including a port assembly defining the port chamber, the steps including sensing a pressure change in the port chamber, and determining whether the sensed pressure change is indicative of fluid flow into or out of the port chamber.

Another embodiment may be an implantable infusion device including a housing, a port assembly defining a port chamber, the port assembly being disposed in the housing such that the chamber is accessible by a needle inserted through the exterior of the housing, a pressure sensor in fluid communication with the port chamber, and electronics disposed in the housing and operably coupled to the pressure sensor, the electronics including a computer readable medium containing instructions that when implemented cause the device to detect, via the pressure sensor, a pressure fluctuation in the port chamber associated with a status of fluid flow into or out of the port chamber.

Another embodiment may be a method including inserting a needle into a patient to access a port chamber defined by a port assembly of an infusion device implanted in the patient, the port chamber being accessible from an exterior of the infusion device and being fluidly connected to a reservoir contained in the infusion device, sensing a pressure change in a port chamber or the reservoir, determining whether the sensed pressure change is indicative of a fluid flow status, and generating a sensory cue if the sensed pressure change is indicative of a fluid flow status.

Figure 1:
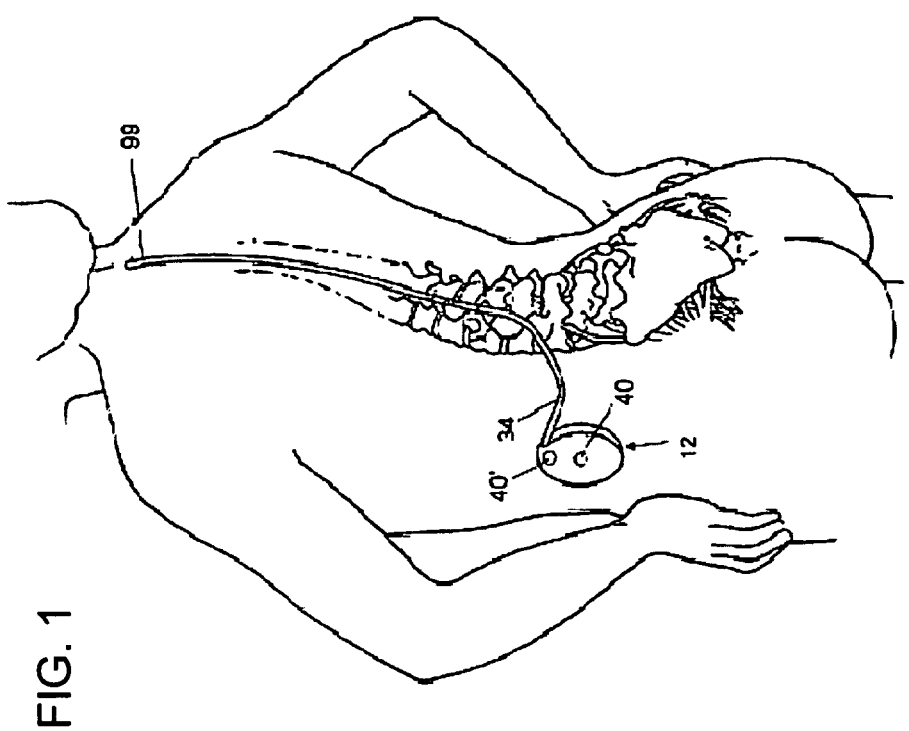
FIG. 1 is a diagrammatic representation of a perspective view of an implantable infusion system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "sensory cue" means a cue capable of being received by a person, such as an audible, tactile, or visual cue. A visual cue may include, for example, text or an image.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4.0, and 5.0) and any range within that range.

The present disclosure describes, inter alia, systems, devices and methods that can be used to detect the withdrawal and filling of a reservoir in an implantable medical device. Furthermore, the systems, devices and methods can detect when the reservoir reaches a substantially empty state or a substantially full state. As discussed herein, it has been discovered that a decrease in pressure can be detected when the therapeutic substance, or other material such as a wash or rinse aid, (collectively "material" or "fluid"), is being withdrawn from the reservoir or has been completely withdrawn using a needle or other device that accesses a port chamber. It has also be discovered that an increase in pressure can be detected when the reservoir is being filled or when the chamber becomes fully or substantially filled.

Referring to FIG. 1, an implantable infusion device 12 having a port assembly 40, 40' is shown implanted in a patient. In the present embodiment, the infusion device 12 is implanted in the side of the patient's abdomen but may, in other embodiments, be implanted in different areas of the body. In one example the infusion device may be implanted in the pectoralis area or in the buttocks. Of course, infusion device 12 may include one, two, three, or any number of port assemblies.

As shown in FIG. 1, a catheter 34 is connected to infusion device 12. Distal portion 99 of catheter 34, which may include one or more openings through which fluid can flow and may be positioned at or near a target location to deliver fluid from infusion device 12 to target location. The target area depicted in FIG. 1 is the patient's spinal canal. However, it will be understood that any region of a patient's body may serve as a target area depending on the conditions, disease, or disorder to be treated. Port assemblies 40, 40' can be accessed percutaneously by a needle (not shown in FIG. 1), through which fluid may be delivered to infusion device 12.

Infusion device 12 may be any device capable of delivering fluid to a patient. For example, infusion device 12 may be an access port, e.g. a vascular access port, through which bolus injections are delivered through a catheter to a patient. Infusion device 12 may also be a device having a reservoir for holding solutions containing therapeutic substances to be delivered over a period of time. Devices that deliver therapeutic substances over time may contain fixed or variable rate pumps, programmable pumps, or the like. An infusion device 12 having a reservoir will generally include a port assembly to allow for refilling of the reservoir.

The infusion device 12 shown in FIG. 1 has two port assemblies 40, 40' one of which may be a catheter access port 40' and one of which may be a reservoir fill port 40. One exemplary device having a catheter access port and a reservoir refill port is Medtronic's SynchroMed® II implantable infusion device. In addition, virtually any other currently known or future developed implantable infusion device can also be used in connection with principles described herein.

While the discussion presented herein is primarily directed to infusion devices for delivering therapeutic substances to a patient, it will be recognized that the principles described herein may be advantageously applied to devices having port assemblies for the withdrawal of fluid from a patient.

Figure 2:
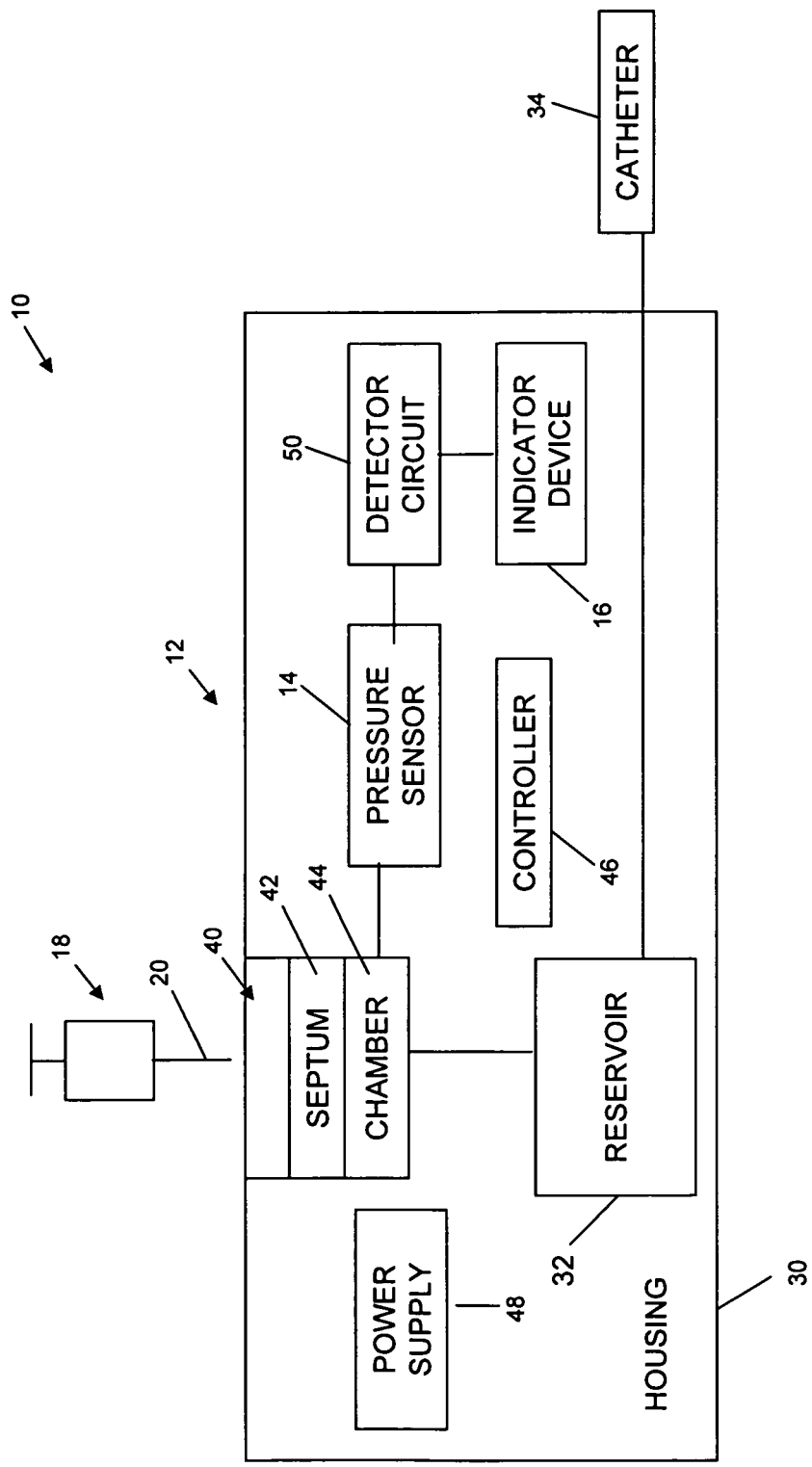
FIGS. 2-8 are block diagrams depicting implantable infusion systems or components thereof in accordance with principles of the present invention.

Referring to FIGS. 2-8B, various embodiments of systems and components thereof are shown in block form. FIG. 2 refers to a representative system 10 that includes an implantable infusion device 12, a pressure sensor 14, and an indicator device 16. Also depicted in FIG. 2 is a syringe assembly 18 including a needle 20 useful for percutaneously interfacing with the implantable infusion device 12. Infusion device 12 shown in FIG. 2 may include a housing 30 that maintains a reservoir 32. Reservoir 32 is designed to contain a therapeutic substance to be delivered to the patient, for example, via a catheter 34. The reservoir 32 may be a constant pressure reservoir, such as a bellows, and maybe fitted with an over pressure mechanism (not shown) that disrupts and shuts off the in-flow if the pressure exceeds a pre-determined threshold.

The therapeutic substance can be any infusion agent, product, or substance intended to have a therapeutic effect such as pharmaceutical compositions, genetic materials, biologics, and others (e.g., insulin, saline solution, fluoroscopy agents, etc.). Regardless, a pump and/or metering device (or "flow regulator") (not shown) can be provided for dictating a flow of the therapeutic substance from reservoir 32 in a desired fashion. The pump/metering device can assume a variety of forms, and device 12 can further include a propellant chamber (not shown) associated with reservoir 32 for exerting a constant, positive pressure onto the reservoir 32 therapeutic substance to ensure delivery to the outlet catheter 34. In other embodiments, the pump/metering device can be eliminated.

In the present embodiment, infusion device 12 may include a fill port assembly 40 fluidly connected to, and otherwise defining an inlet of, reservoir 32. In more general terms, however, fill port assembly 40 may assume a conventional configuration whereby a septum 42 seals a port chamber 44 relative to an exterior of the housing 30. Port chamber 44, in turn, is in fluid communication with reservoir 32 (e.g., a permanent fluid connection is established and a valve means is provided that actuates to selectively fluidly connect port chamber 44 and reservoir 32, etc.). Needle 20 may percutaneously deliver a liquid to port assembly 40, and in particular through septum 42 and into port chamber 44, as part of a reservoir 32 refilling operation. The therapeutic substance may then be pushed to the reservoir 32. In the present embodiment, the pressure in the reservoir 32 is less than ambient atmospheric pressure and so the needle 20 does not need to be actuated but rather the ambient atmospheric pressure initiates and sustains the flow of fluid into the reservoir 32. In further embodiments pressure may be placed on a plunger of the syringe and therefore a higher pressure may be exerted on the reservoir.

Figure 3:
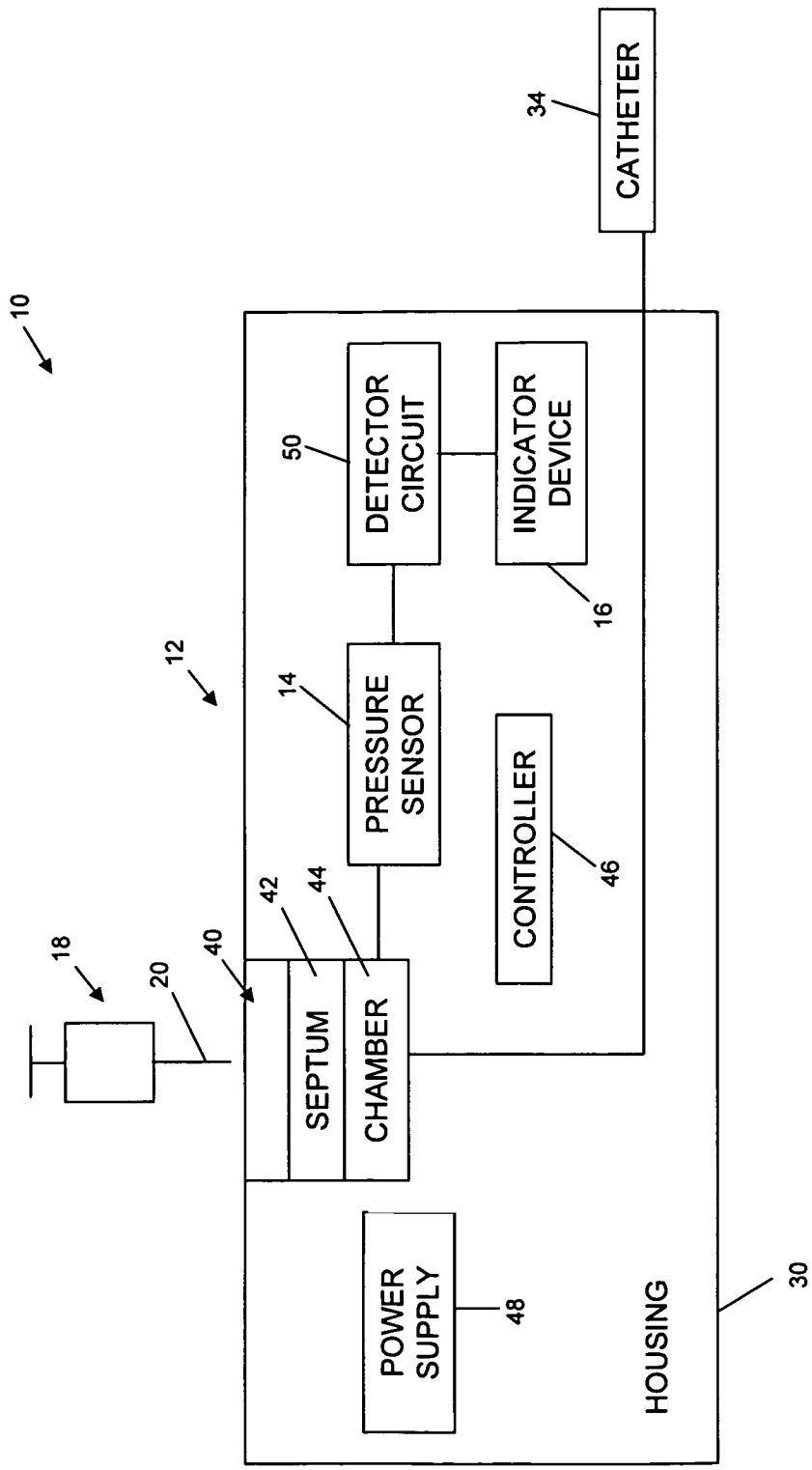

Referring to FIG. 3, an infusion device 12 without a reservoir is shown. In the embodiment shown in FIG. 3, as with the embodiment depicted in FIG. 2, port chamber 44, defined by port assembly 40, is accessible by needle 20 through septum 42. Port chamber 44 is in fluid communication with catheter 34 such that therapeutic substance infused through needle 20 into port chamber 44 will be delivered directly to a target area of a patient through catheter 34. Such a system may allow for a bolus of therapeutic substance to be directly administered.

Regardless of the embodiment depicted, infusion device 12 may include additional components as known conventionally or developed in the future. For example, infusion device 12 can include a controller 46 or other electronics, for example in the form of a digital microprocessor, although any equivalent device may be substituted for a digital microprocessor; in many instances, it may also be desirable that the controller 46 includes data storage capabilities. Where provided, the controller 46 (as well as other components) can be powered by a power supply 48 (that may be preferably in the form of a battery or other self-contained power source). Other components can further be provided with infusion device 12 that are not otherwise illustrated, such as safety valves, flow restrictors, etc., that may enhance operation of the infusion device 12.

Figure 4:
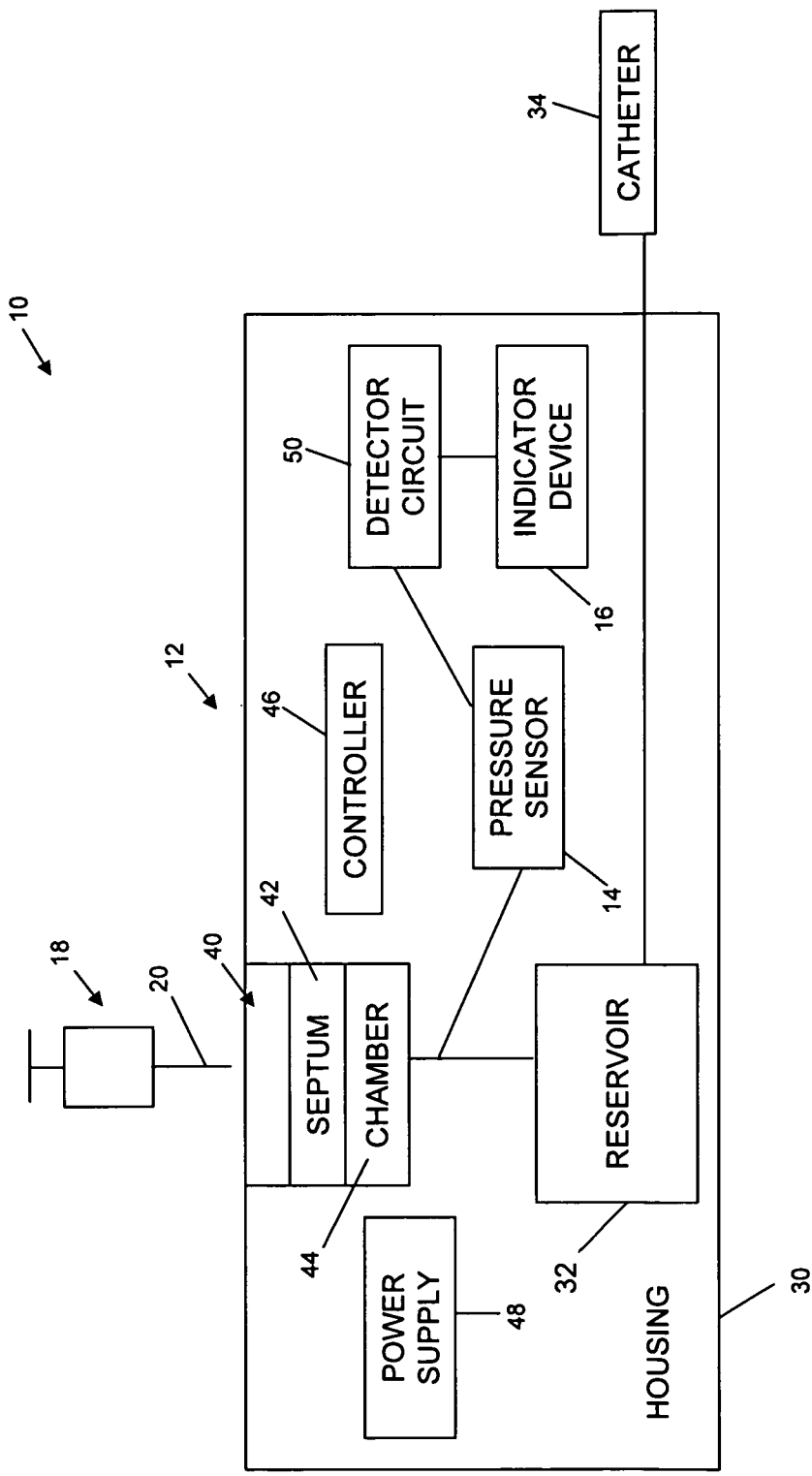

With the above general construction of the infusion device 12 in mind, a pressure sensor 14 may be maintained by housing 30, and may be operably situated between port assembly 40 and reservoir 32 (see, e.g., FIG. 4). The pressure sensor may detect pressure changes in between the chamber 44 and the reservoir 32. In further embodiments, pressure changes may be detected in reservoir 32. In various embodiments, pressure sensor 14 sends pressure-related information to a detector circuit 50 that in turn may prompt operation of an indicator device 16 (see further description below).

As depicted in the embodiments shown in FIGS. 2-4, detector circuit 50 and indicator device 16 may be included in housing 30. Detector circuit 50 may be adapted or programmed to prompt operation of indicator device 16 based upon pressure-related information generated and signaled by pressure sensor 14. For example, detector circuit 50 can be configured or programmed to prompt operation of indicator device 16 upon determining (e.g., using a logic circuit, a comparator, etc.) that the pressure sensed by the pressure sensor 14 (or as otherwise indicated by information signaled from the pressure sensor 14) is indicative of fluid being withdrawn or added to the reservoir 32. In addition, the pressure sensed by the pressure sensor 14 may be interpreted by the detector circuit 50 as indicating the reservoir 32 is empty or full (see below). In the embodiments shown in FIGS. 2-4, detector circuit 50 is shown as being a component apart from controller 46. In other embodiments, however, detector circuit 50 can be provided with the controller 46 such that the controller 46 is programmed to operate indicator device 16 in a desired fashion. In yet other alternative embodiments, detector circuit 50 can be eliminated.

Figure 5:
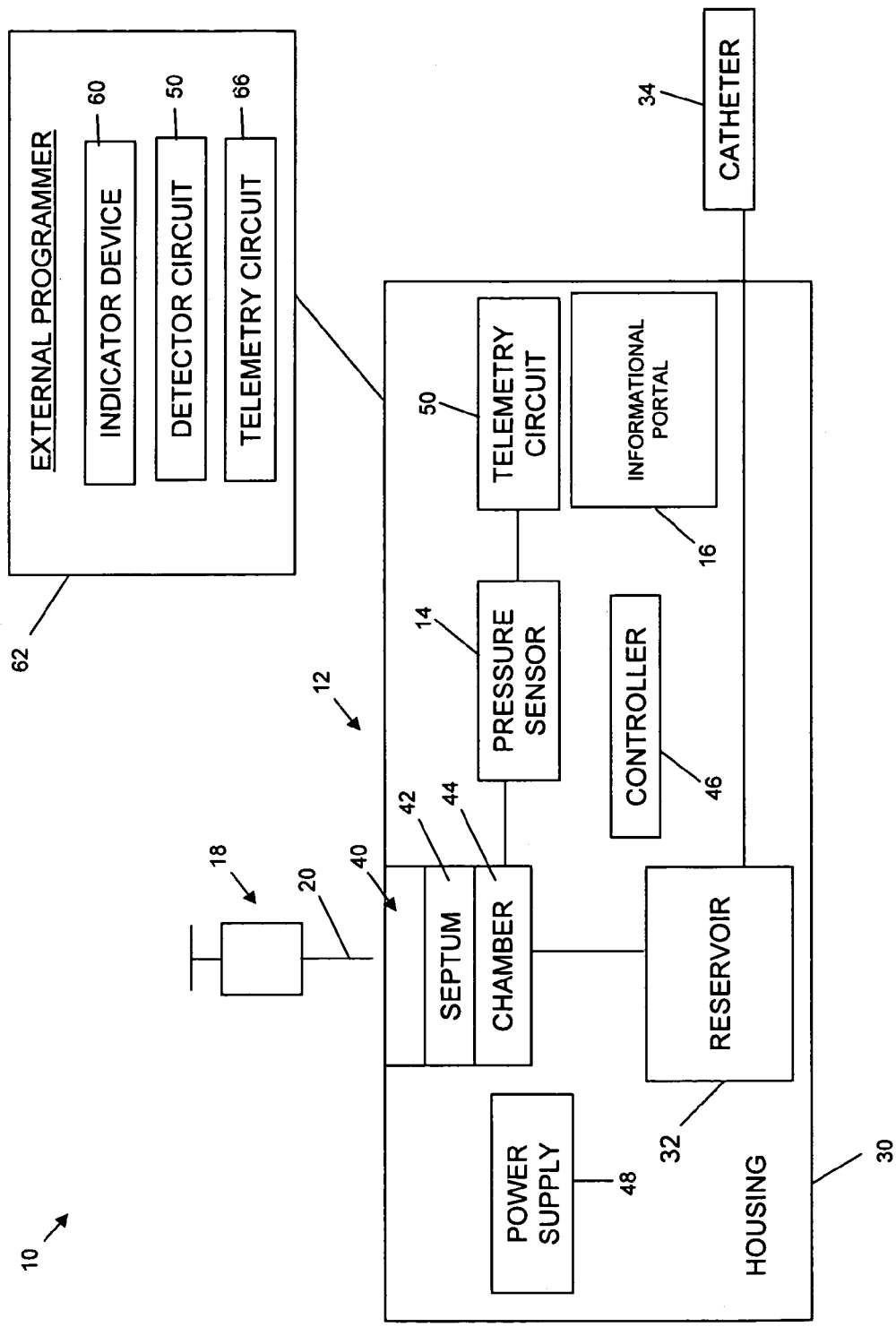

With reference to the embodiments depicted in FIGS. 2-4, indicator device 16 is capable of relaying information to the user, either through an auditory or visual clue, or by transmitting information to an external programmer. For example, FIG. 5 is a block diagram representing a representative system 10 that is similar in many respects to the system 10 depicted in FIG. 2. However, with the embodiment depicted in FIG. 5, indicator device 60 is located apart from housing 30, for example, as part of an external programmer 62. External programmer 62 is adapted to communicate with infusion device 12 through the patient's skin such that in various embodiments, external programmer 62 and infusion device 12 are in wireless communication. Communication may be established via telemetry circuitry 64 maintained by the housing 30 and corresponding telemetry circuitry 66 maintained by the external programmer 62 (or a component (e.g., a handheld instrument) electronically coupled to external programmer 62). Alternatively, other forms of wireless or wired communicative links between infusion device 12 and external programmer 62 can be provided.

In various embodiments, pressure sensor 14 is electronically coupled to telemetry circuitry 50 (for example, via a controller (not shown)), with pressure-related information generated by pressure sensor 14 being signaled to external programmer 62. External programmer 62 may include a detector circuit 50 and a logic circuit that interprets and then displays the information collected by the pressure sensor 14.

The parameters under which detector circuit 50 will prompt operation of the indicator device 60 are described in greater detail below. In one embodiment, indicator device 60 is a display screen adapted to display information to the clinician. As is known in the art, a display screen is commonly provided with an external programmer 62 (e.g., an N'Vision™ Programmer available from Medtronic, Inc., of Minneapolis, Minn. as part of the SynchroMed® II Infusion System), and can display information in a variety of fashions, for example, with text, pictures, symbols, graphical information, etc. Indicator device 60 can further include a sensory cue generator, such as sound generator, as previously described. In one embodiment, upon determining that pressure-related information generated by pressure sensor 14 is indicative of some flow state of the therapeutic substance, detector circuit 50 prompts indicator device 60 to inform the clinician via the display screen, sound generating device, or the like. In other embodiments, detector circuit 50 can be eliminated with indicator device 60 simply displaying a current pressure reading provided by the pressure sensor 14. Under these conditions, the clinician can make a self-evaluation as to whether the sensed and displayed pressure is indicative of withdrawal, fill, empty, or full states.

Figure 6:
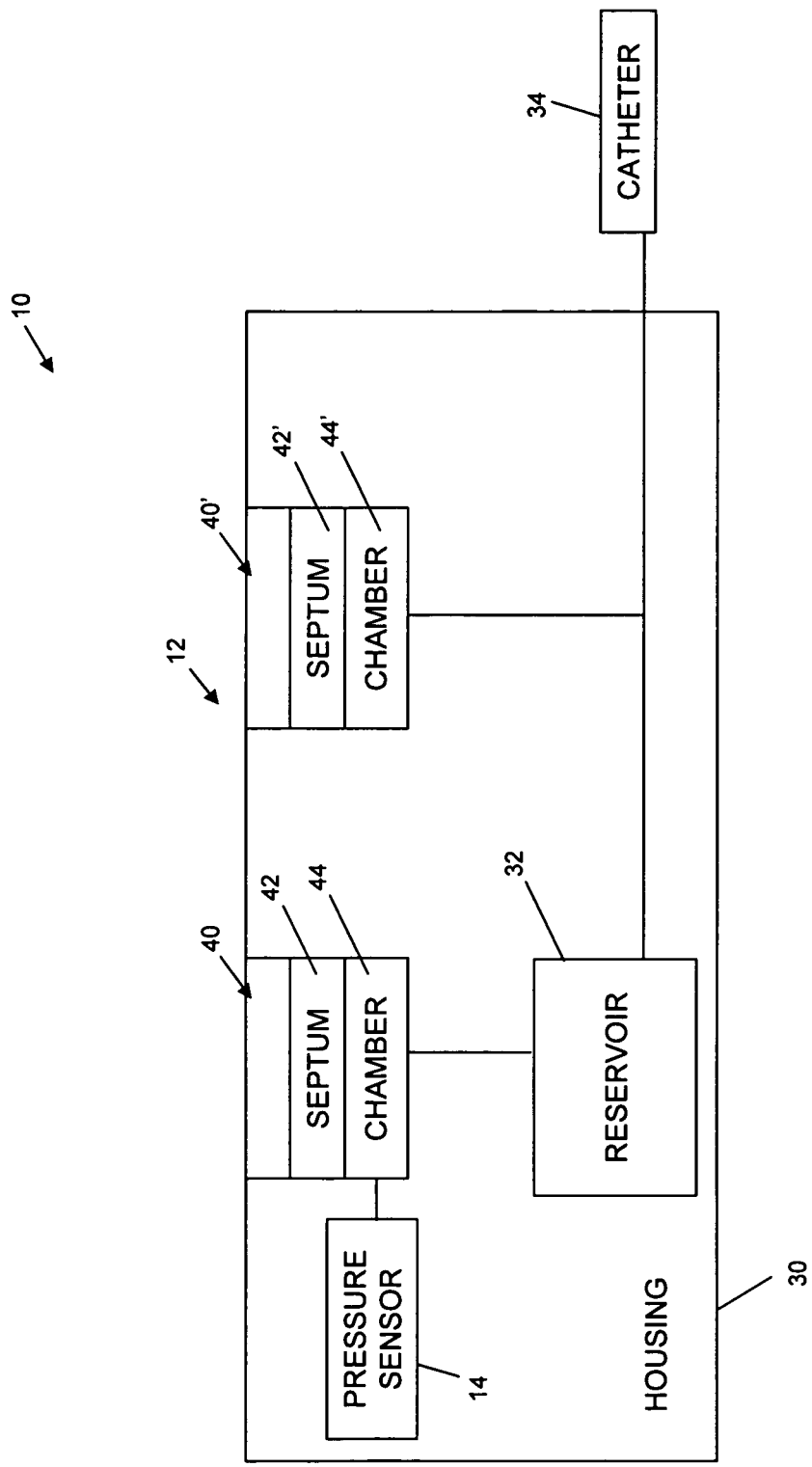
Figure 7:
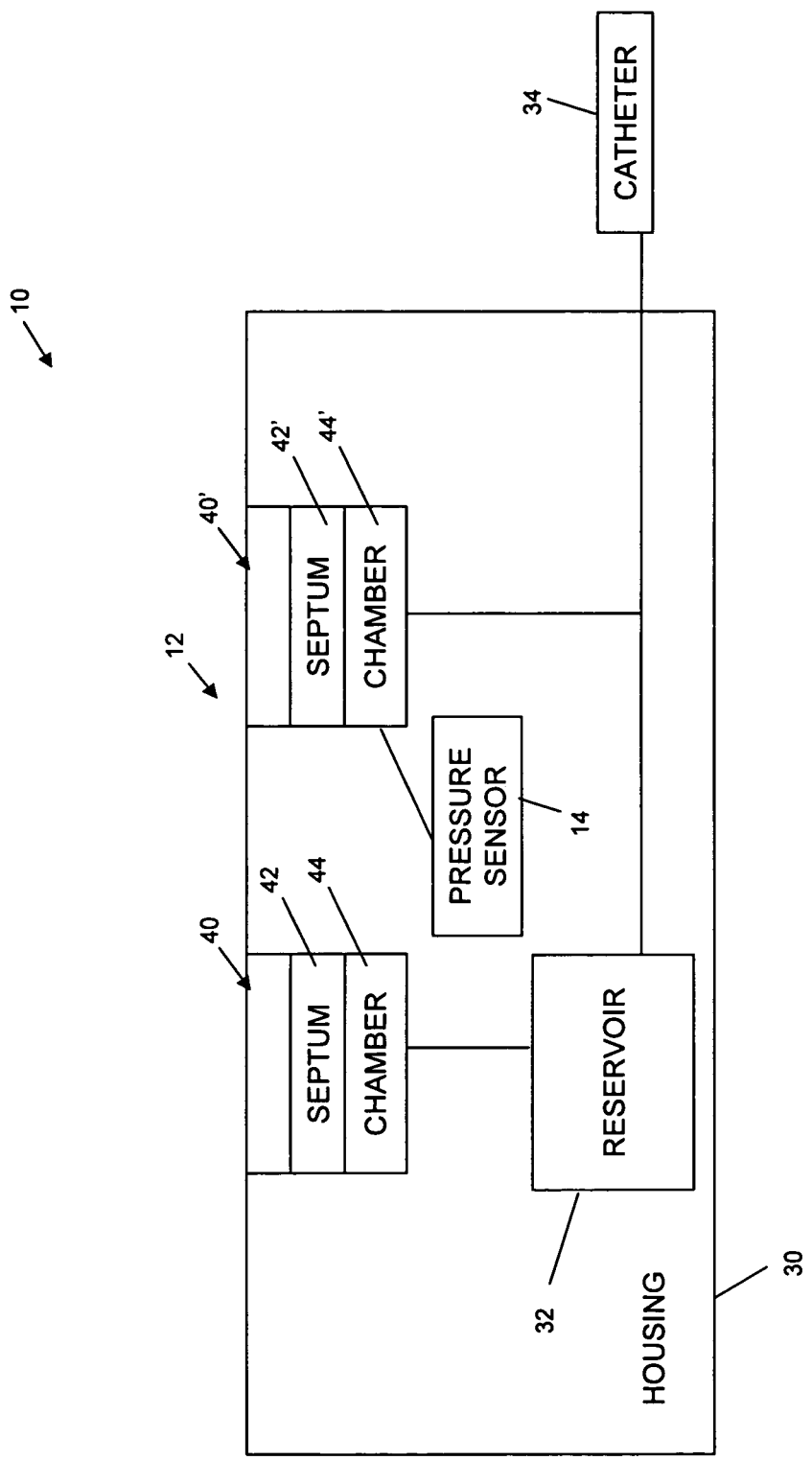
Figure 8:
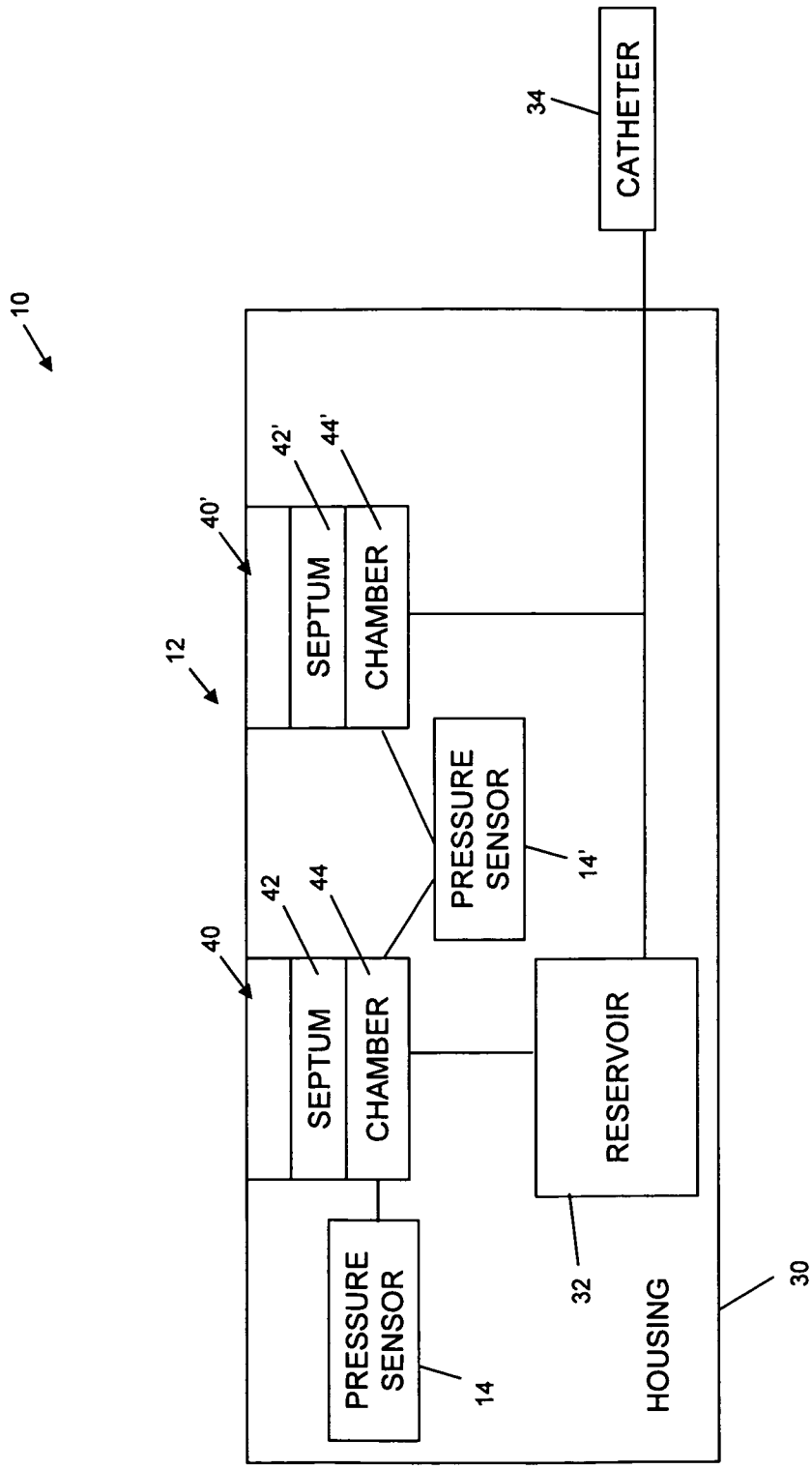

With the above description in mind, FIGS. 6-8 show alternative embodiments of system 10 in block form. While FIGS. 6-8 do not show some of the features of the devices described in FIGS. 2-5, it will be understood that one or more of the features discussed above may be included. System 10 as shown in FIGS. 6-8 may include two port assemblies 40, 40'. Port assembly 40 is a refill port assembly in fluid communication with reservoir 32, and port assembly 40' is a catheter access port assembly in fluid communication with catheter 34. Pressure sensor 14, 14' may be in fluid communication with fill port chamber 44 (FIG. 6), or the catheter access port chamber 44' (FIG. 7), or both (FIG. 8). The pressure sensor 14' may also be in direct fluid communication with the fill port chamber 44 and catheter access port chamber 44' (FIG. 8) or in communication with the passage connecting the fill port chamber 44 or catheter access port chamber 44' with the reservoir 32 or the catheter 34 (not shown). In addition, the pressure sensor 14, 14' may be in any portion of the infusion pump 12 so as to enable detection of a pressure indicative of a fluid status during filling or emptying of the reservoir or during bolus injection.

Figure 9:
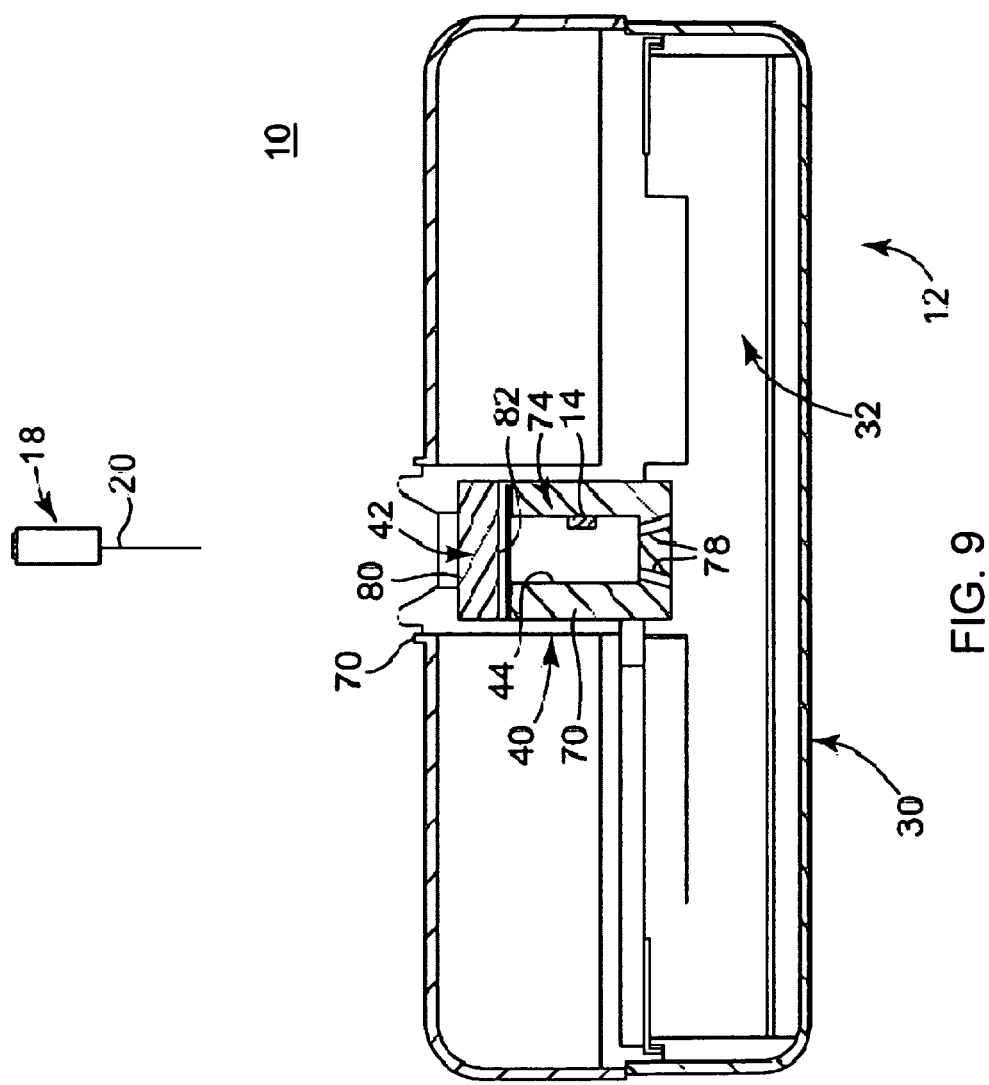
FIG. 9 is a cross-sectional view of a portion of an implantable infusion device useful with the systems of FIGS. 2-8.

FIG. 9 is a simplified, cross-sectional view of an embodiment of a portion of system 10, such as the pressure sensor 14 in conjunction with relevant portions of the infusion device 12, such as housing 30, reservoir 32, and the port assembly 40. In general terms, port assembly 40 is formed in an opening 70 of housing 30 such that port assembly 40 is exteriorly accessible relative to housing 30. Septum 42 is disposed across port chamber 44 (referenced generally) defined by a wall of port assembly 40, such that septum 42 seals the opening 70 relative to the port chamber 44/reservoir 32. Septum 42 can be manufactured of any suitable material or materials. Typically, septum 42 will be made of elastomeric materials, for example, silicone rubber, that are pierceable by needle 20 (which itself does not necessarily form a part of the system 10) and compatible with the therapeutic substance (not shown) to be contained with reservoir 32.

In various embodiments, port assembly 40 may further include a septum plug 74 used to retain septum 42 while providing a fluid-tight seal. Septum plug 74 may define the port chamber 44 to include drain holes 78 that allow fluids delivered to port chamber 44 to pass into reservoir 32. In some embodiments, a valve feature (not shown) can be provided to further control flow of liquid from port chamber 44 to reservoir 32 as is known in the art. In still further embodiments the drain holes 78 may lead to a passage (not shown) that then leads to the reservoir 32. The septum 42 may define a first exterior side 80 and a second or interior side 82. Exterior side 80 is exposed relative to opening 70 of housing 30, whereas interior side 82 defines a portion of port chamber 44. While FIG. 9 is described with regard to a fill port assembly 40, it will be understood the components described with regard to FIG. 9 can be readily applied or adapted to the catheter access port assembly.

With the above conventions in mind, pressure sensor 14 may, in various embodiments, be associated with port assembly 40, and in particular port chamber 44, by placing the pressure sensor 14 along an interior of a wall of septum plug 74. In other embodiments, pressure sensor 14 may be disposed within a thickness of septum plug 74 (such as by forming (e.g., overmolding) septum plug 74 about pressure sensor 14). Even further, pressure sensor 14 may be assembled to an exterior of septum plug 74 (relative to the port chamber 44). In further embodiments the pressure sensor 14 is placed in the drain holes 78 or the passage that lead to the reservoir 32.

Pressure sensor 14 may be a variety of different forms. For example, pressure sensor 14 may be a capacitive measurement device which determines pressure by measuring the change in capacitance of a flexible membrane attached but insulated from a conductive, gas-filled cavity due to deflections caused by pressure applied over the flexible membrane. Alternatively, pressure sensor 14 may be a sensor that utilizes the piezo-electric effect or resistive change due to metallic strain in order to measure pressure applied. Regardless of the specific manner in which pressure sensor 14 measures pressure, in various embodiments, pressure sensor 14 is adapted to generate a signal indicative of a pressure of port chamber 44. Alternatively, pressure sensor 14 may be adapted to generate a signal indicative of a change in pressure of port chamber 44. Pressure sensor 14 may be any device capable of sensing and signaling information indicative of pressure characteristics associated with port chamber 44 or the passage between the port chamber 44 and the reservoir 32. Pressure sensor 14 may be electronically coupled to detector circuit 50 or indicator device 16, 60 in a variety of ways. For example, electrical wiring (not shown) can provide the desired electrical connection. Alternatively, a wireless link may be provided between pressure sensor 14 and the processing device and/or display device selected.

In general terms and without being bound by the following description, it is believed that withdrawal or filling of therapeutic substance from the reservoir 32 causes the pressure profile existing in the fluid system to fluctuate from a normal state. In addition, when the reservoir 32 reaches an empty or full state, or a substantially empty or full state, or when the needle 20 is inserted or when clamps are opened and closed, the pressure profile may also change.

Figure 10:
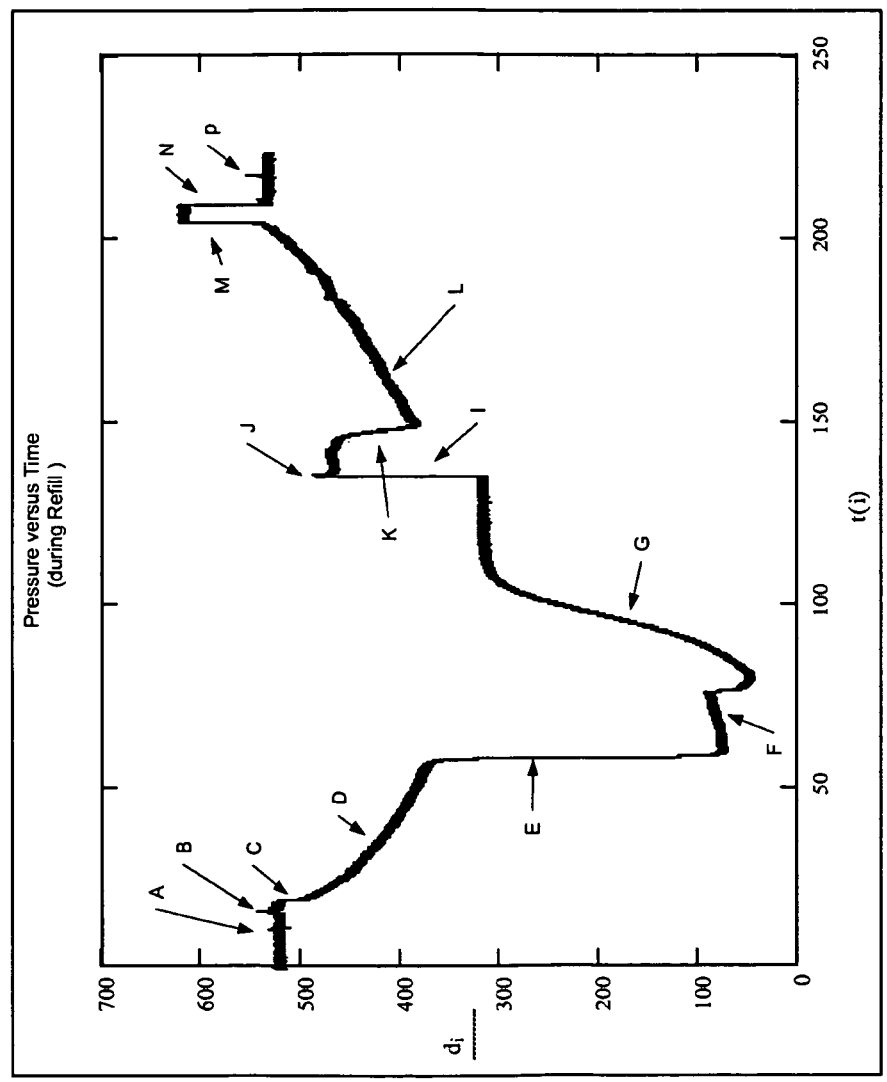
FIG. 10 is a graph of pressure over time as monitored in a reservoir of an implantable infusion device during filling and emptying of the reservoir.

Referring to FIG. 10, an exemplary pressure profile of withdrawing fluid from the reservoir 32 will be described. Withdrawal may be undertaken when the therapeutic substance kept in the reservoir 32 is being removed. Afterward the reservoir 32 can be filled with the newly selected therapeutic substance. In some cases this may be the same therapeutic substance at a different concentration. In other cases it may be a different drug or an entirely different type of material. In still further situations the reservoir 32 may first be filled and rinsed with a different material before the new therapeutic substance is placed therein. The pressure profile shown in FIG. 10 can be obtained using any of the example systems 10 described above. Moreover, variations on the pressure profile may be obtained depending on whether a reservoir 32 is being accessed for emptying and/or filling or whether a catheter 34 is being accessed for a bolus injection. As described below, the indicated pressure may indicate a fluid flow status that is indicative of the direction of the fluid flow and how much fluid is left in the reservoir 32 or the port chamber 44.

The pressure profiles depicted in FIG. 10, were obtained by continuously sampling the pressure of the refill septum port of a prototype, bellows-based reservoir pump over the course of an entire refill procedure.

The normal pressure indicated by the pressure sensor 14 in the present embodiment infusion pump 12 is approximately 490 mmHg (about 9.5 pounds per square inch (psi)) as the present embodiment infusion pump 12 is a negative pressure pump wherein the fluid in the reservoir 32 and the port chamber 44 are kept at a pressure below normal atmospheric pressure, about 760 mmHg (about 14.7 psi). Position A on the graph shows a pressure spike when the needle 20 is inserted into the port chamber 44. In the present embodiment, the needle is connected to a tubing or hose that, during the initial insertion, is clamped off from a needle reservoir into which the fluid from the reservoir 32 will be drained or from which the fluid will be placed into the reservoir 32. Position B indicates another pressure spike when the clamp on the tubing separating the needle 20 from the needle reservoir is unclamped or released. In the presently described method the needle reservoir is empty and the fluid in the infusion pump 12 reservoir 32 will be removed before new fluid with therapeutic substance contained therein is placed therein.

As illustrated at point C, when the syringe is withdrawn to create a low pressure in the needle reservoir and to draw the fluid from the reservoir 32, a relatively rapid drop in pressure is detected by the pressure sensor 14. Fluid will begin to flow out of the reservoir 32 and the port chamber 44 at a steady rate that depends on the degree of low pressure created in the needle reservoir. Point D on the pressure graph illustrates a pressure decrease during the withdrawal, or aspiration, phase, of the fluid from the reservoir 32.

As may be appreciated, the steady state infusion pump 12 reservoir 32 will try to compensate and maintain the pre-programmed pressure in the reservoir 32. As the reservoir empties, the pressure will drop, but within a specific range as shown at point D. Therefore, the pressure will slowly drop as shown at point D. However, at some point the reservoir 32 will no longer be able to maintain the pressure as too little fluid will remain in the reservoir 32. When the reservoir 32 is at or near an empty state, the reservoir 32 and pressure compensation system of the infusion pump 12 may no longer be able to keep an elevated pressure, and the pressure will quickly drop as illustrated at point E. In the present embodiment the reservoir 32 may undergo the non-linear pressure behavior illustrated in FIG. 10 at point E when at or near the empty state. Point F illustrates the pressure stabilizing in the empty reservoir 32 and the port chamber 44 at some reduced pressure depending on the relative low pressure being exerted by the syringe. At point F the tubing is clamped for removal of the first syringe and connection of a refill syringe to the tubing.

Point G illustrates a relatively slow increase in the detected pressure towards the nominal pressure after the reservoir 32 is emptied and the tubing has been clamped. The increase in the detected pressure may be in part due to the inability of the pump to perfectly hold a vacuum. Micro amounts of gas may permeate through the septum.

Point I illustrates where the tubing is unclamped such that the pressure from the refill syringe containing fluid for filling the reservoir 32 is transferred to port chamber 44 and reservoir 32 and detected by the pressure sensor 14. At point J a rapid rise in pressure is shown. In the present embodiment, the pressure in the fluid in the refill syringe is at atmospheric pressure. The pressure inside the reservoir 32 is set below this and so as the atmospheric pressure (760 mmHg) of the fluid enters the reservoir 32 the reservoir tries to compensate and return to the lower selected pressure. Point K shows the reservoir and propellant equalizing the pressure back to the predetermined nominal state. However, in present embodiment the pressure may slowly rise such as at point L as the reservoir 32 is filled. As may be appreciated, if pressure were to be applied to a syringe plunger to increase the flow rate into the infusion pump 12, the pressure exerted may be significantly higher.

In the present embodiment, when the reservoir 32 has expanded to such a point wherein the pressure in the reservoir 32 exceeds some predetermined level, an over pressure mechanism may engage to stop the flow of fluid into the reservoir 32. Point M shows the pressure spike as the reservoir reaches a full state. Point N is the point at which the clamp on the tubing is reset. The pressure detected may then fall again as the reservoir continues to work to adjust the internal pressure to that selected level. Point P shows where the needle 20 is removed and the filling operation is complete.

As can be seen from FIG. 10, during filling of the reservoir, an increase in pressure is observed. Again, because in the present embodiment the pump is a constant pressure pump the reservoir 32 and propellant gases will try to compensate for the rise in fluid by expanding (the reservoir 32) and reducing the pressure placed on the reservoir 32 by the propellant gas. However, there will still be a measurable increase in pressure during the time in which the reservoir 32 is being filled due to the compensation lag. As previously mentioned, the present embodiment is used with a constant pressure reservoir. One example of such a reservoir includes an accordion shaped reservoir body (which may be described as a bellows shape) surrounded by propellant gasses that keep the pressure inside the reservoir 32 constant. However, some pressure differentiation, i.e., higher or lower pressure, will occur as fluid is withdrawn as the propellant gases try to "catch up" the reservoir 32 to the pre-set reservoir 32 pressure. This may result in different pressure profiles depending on the type of system. However, still detectable pressure changes may still be indicative of fluid flow status.

Figure 11:
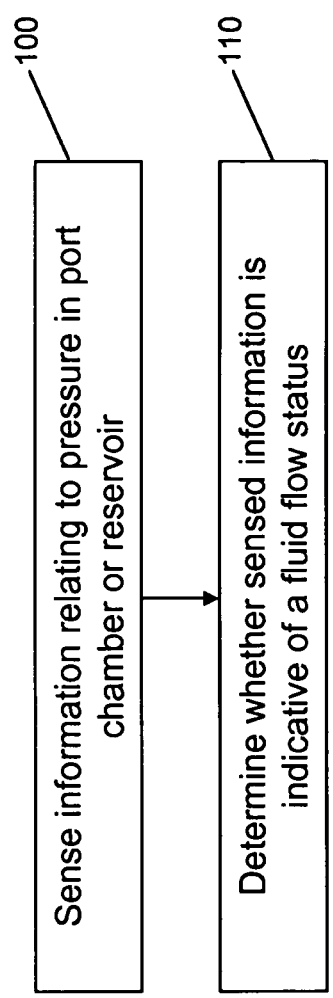
FIGS. 11-12 are flow diagrams of representative methods in accordance with the principles of the teachings herein.

In light of the above, FIG. 11 provides a flow diagram illustrating a method for monitoring the fluid flow in infusion device 12. The method includes sensing information relating to pressure in a port chamber (100) and determining whether the sensed information is indicative of fluid flow into or out of port chamber (110).

Figure 12:
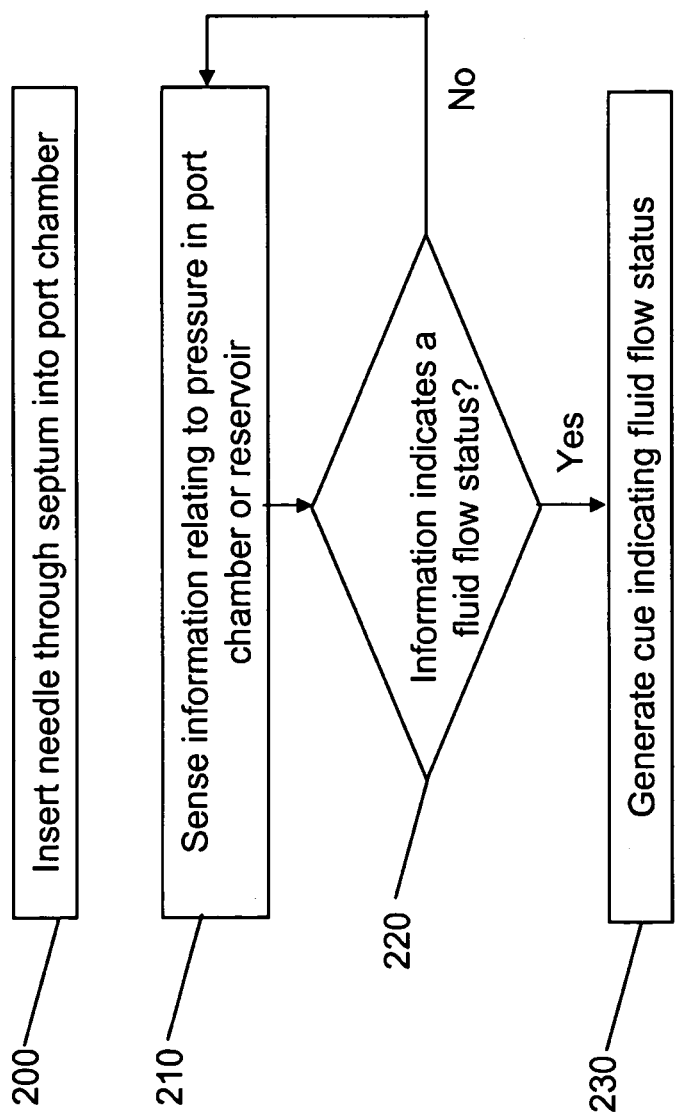

With the above discussion in mind, FIG. 12 provides a flow diagram illustrating another method for monitoring the withdrawal or filling of fluid. The method includes inserting a needle into a patient in an attempt to access a port chamber of an infusion device (200) and sensing information relating to pressure in the port chamber or the reservoir (210). A determination may then be made as to whether the sensed information is indicative of a fluid flow status (220), such as withdrawal of fluid, addition of fluid, or a substantially empty or full reservoir. If the sensed information is indicative of a fluid flow status, a cue may be generated to indicate the detected status (230). If the sensed information is not indicative of a fluid flow status, a cue will not be generated and the clinician may then again attempt to start withdrawal or filling of the fluid (200).

One of skill in the art will understand that components or steps described herein regarding a given embodiment or set of embodiments may readily be omitted, substituted, or added from, with, or to components or steps of other embodiments or sets of embodiments, as appropriate or desirable.

What is claimed is:

1. A method for detecting fluid flow into and out of an implantable infusion device, the device including a refill port assembly defining a port chamber and a reservoir in communication with the port chamber, the method comprising:
    inserting a needle into the port chamber and one of dispensing a fluid into the port chamber or withdrawing a fluid out of the port chamber;
    sensing, via a sensor in fluid communication the port chamber, a pressure change in the port chamber due to one of dispensing a fluid into the port chamber and withdrawing a fluid out of the port chamber; determining a fluid flow status based on whether the sensed pressure change is indicative of fluid flow into or out of the port chamber, wherein the fluid flow status is one of a substantially full reservoir or a substantially empty reservoir; and
    generating a sensory cue based on the fluid flow status.

2. The method of claim 1, further comprising:
    generating a first sensory cue if the sensed pressure change is indicative of fluid flow into the port chamber.

3. The method of claim 1, further comprising:
    generating a second sensory cue if the sensed pressure change is indicative of fluid flow from the port chamber.

4. The method of claim 3, wherein generating the sensory cue comprises generating an audible cue.

5. The method of claim 3, wherein generating the sensory cue comprises generating the sensory cue from a second device, the second device being in wireless communication with the infusion device.

6. The method of claim 5, wherein generating the sensory cue from the second device comprises generating the cue from a programmer device.

* * * * *